(12) United States Patent
Cronin et al.

(10) Patent No.: US 7,858,035 B2
(45) Date of Patent: Dec. 28, 2010

(54) METHOD FOR CLEANING IN-PROCESS SENSORS

(75) Inventors: James Timothy Cronin, Townsend, DE (US); Thomas Shields Elkins, Waverly, TN (US); Lisa Edith Helberg, Middletown, DE (US); Angela Ruth Strzelecki, Boothwyn, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/881,440

(22) Filed: Jul. 27, 2007

(65) Prior Publication Data

US 2007/0269366 A1 Nov. 22, 2007

Related U.S. Application Data

(62) Division of application No. 10/256,672, filed on Sep. 27, 2002, now Pat. No. 7,300,630.

(51) Int. Cl.
*G01N 33/00* (2006.01)
(52) U.S. Cl. ........... 422/68.1; 422/82.05; 422/82.09; 422/99; 422/102
(58) Field of Classification Search ............ 422/68.1, 422/82.05, 82.09, 99, 102
See application file for complete search history.

(56) References Cited

U.S. PATENT DOCUMENTS

| | | | |
|---|---|---|---|
| 4,040,473 A | 8/1977 | Wheeler | |
| 4,307,741 A | 12/1981 | Rossi | |
| 4,383,572 A | 5/1983 | Bellows | |
| 4,385,936 A | 5/1983 | Rossi | |
| 4,874,243 A | 10/1989 | Perren | |
| 5,185,531 A | 2/1993 | Wynn | |
| 5,638,172 A * | 6/1997 | Alsmeyer et al. | 356/301 |
| 6,562,312 B2 | 5/2003 | Cronin et al. | |
| 6,753,186 B2 * | 6/2004 | Moskoff | 436/125 |
| 7,250,302 B2 | 7/2007 | Bernhardsson et al. | |
| 7,300,630 B2 | 11/2007 | Cronin et al. | |
| 2007/0267050 A1 | 11/2007 | Cronin et al. | |

FOREIGN PATENT DOCUMENTS

DE   35 38 313 A1   4/1986

OTHER PUBLICATIONS

U.S. Appl. No. 09/739,597, filed Dec. 18, 2000, Cronin et al.

* cited by examiner

*Primary Examiner*—Sam Siefke

(57) ABSTRACT

A cleaning system and method for in-process sensors wherein a scouring jet discharges process fluid as the cleaning agent to remove solids and other contaminants from the surface of the sensor.

15 Claims, 1 Drawing Sheet

METHOD FOR CLEANING IN-PROCESS SENSORS

CROSS-REFERENCE TO RELATED APPLICATION

This application is a divisional claiming the benefit of U.S. patent application Ser. No. 10/256,672, filed Sep. 27, 2002, which is incorporated by reference in its entirety.

FIELD OF THE INVENTION

This invention relates to an improved system and method for cleaning of in-process sensors.

BACKGROUND OF THE INVENTION

In-process sensors, such as on-line sensors, are used widely in the chemical, pharmaceutical, and food processing industries to measure one or more characteristics, such as composition, temperature, pressure, or pH of a process fluid. All of these sensors have a surface by which the sensor interacts with the process fluid in order to make the desired measurement. For example, spectroscopic instruments interact with process fluid through some type of optical window. Normal operation of such sensors typically requires that the surface of the sensor be absolutely free of contaminants, such as organic growth, solids, films or coatings, in order to take accurate measurements. For many processes this requirement is difficult to achieve. Therefore, various methods have been developed for cleaning the surfaces of such sensors.

Some methods for cleaning in-process sensors require removing the sensor from service, either by physical removal of the sensor from the process installation or by isolating (valving off) the sensor from the process. Both of these methods can be time consuming, especially if the sensor surface fouls quickly. These methods are potentially dangerous, for example, if the process involves toxic or otherwise hazardous chemicals. These methods may also harm the equipment. Moreover, the process itself, in addition to the process measurement, may be suspended until after cleaning has been completed.

An upgrade to isolation of an in-process sensor for cleaning purposes is available in some systems, wherein a cleaning fluid is directed at the sensor during operation. These systems are limited to those where the process is not detrimentally affected by addition of the cleaning fluid. One example is in waste water treatment where clean, pressurized water and/or air is directed at a sensor for cleaning purposes.

Mechanical methods have also been developed for cleaning of in-process sensors. Such methods involve use of wipers, brushes, and the like to physically scrape contaminants off the sensor. Disadvantages of these methods include limited use with viscous process streams, the necessity to suspend the process measurement, and difficulty in designing a mechanical cleaning device into the process equipment, especially for a process containing corrosive or otherwise hazardous streams.

Ultrasound has been applied to cleaning of in-process sensors. The use of ultrasound generates cavitation near the sensor to remove solids. However, ultrasound is limited to use with low solids and viscosity process streams, at pressures below 100 psig, certain temperatures, and streams with low specific gravity.

U.S. Pat. Nos. 4,307,741 and 4,385,936 disclose an apparatus and a process for cleaning a probe inserted into a sample process stream. The apparatus comprises a canister containing a cleaning agent, from which the cleaning agent is discharged, mixed with water and pumped through a nozzle with a jet spray end directed at the probe. The method is described as an improvement over cleaning methods that involve (1) removal of a probe from a process, (2) use of ultrasound to vibrate process fluid as it passes the probe and (3) use of brushes and/or wipers while the probe is in service. Nevertheless, the apparatus and method rely on introduction of a material (i.e., cleaning agent) foreign to the process stream.

U.S. Pat. No. 5,185,531 provides a cleaner for an in-line optical sensor comprising a blade. The blade mechanically wipes the surface of a sensor window. Measurements from the sensor are suspended until the cleaning operation is complete and data re-stabilizes.

German Patent Application DE 35 38 313 A1 discloses a device to clean sensors in bodies of water such as ditches around oil storage tanks, where the sensors are contaminated with animal or plant material. The device is essentially a hose with a nozzle from which a pressurized fluid is discharged so as to impact the external surface of the sensor. The pressurized fluid is water and/or air, which generates bubbles or current in the water, creating an oscillatory motion at the surface of the sensor to remove contaminants.

All of the aforementioned methods include numerous limitations and disadvantages. Therefore, it is desirable to have a cleaning system for in-process sensors, that allow for in situ cleaning of the sensor surface while the sensor is in operation, that is, measurement need not be suspended during cleaning. It would further be advantageous to clean the sensor without introducing foreign material, such as cleaning fluids into the process. The present invention meets these needs.

SUMMARY OF THE INVENTION

The present invention provides a cleaning system for an in-process sensor comprising:
(a) a sensor, wherein the sensor has a surface, which is in contact with a process fluid;
(b) a scouring jet having an inlet and an outlet;

wherein the process fluid is in contact with said inlet of the scouring jet and, wherein the jet is positioned relative to the sensor such that discharge from the outlet impinges on the surface of the sensor.

The present invention further provides a method for cleaning an in-process sensor, comprising:
(a) directing at least a portion of the process fluid to a scouring jet; and
(b) discharging said fluid from the scouring jet such that the fluid impinges on the sensor.

The improved cleaning system and method of the present invention are useful in any process where there is present an in-process sensor susceptible to contamination from the sensor's environment, including components of the process stream. The improved cleaning system and method are particularly useful for processes where sensors are exposed to high solids, viscous streams, toxic, corrosive, or otherwise hazardous streams where removal of the sensor, or even isolating the sensor may create dangerous conditions. Furthermore, the system and method are useful for processes that contain highly reactive or hazardous materials, and, where use of even relatively benign cleaning agents such as air and/or water are not possible. In such systems, use of the cleaning system and method are especially advantageous to provide safe, reliable measurements for both continuous and batch processes.

Advantages of the cleaning system and method of this invention include:

- Continuous process operation and sensor operation during cleaning of sensor.
- Use of process fluid avoids introduction of a foreign material into the process.
- Cleaning system is wholly contained within process operations, avoiding the need to remove the sensor to clean.
- Process fluid is never contaminated with non-process cleaning fluid.
- Stringent control of composition of the process fluid is maintained.
- Viscous process fluids can be used.
- Improved safety of operation when process fluid comprises hazardous (toxic, corrosive, highly reactive) materials.
- Sterile conditions are maintained when sensors are used in biological and pharmaceutical systems.
- High level of control over cleaning operation is available by independently adjusting intensity, frequency and duration of scouring.

The improved cleaning system and method are useful in a number of industries wherein in-process sensors are employed. A few examples include chemical processes where the process fluid comprises corrosive, toxic or other hazardous components (e.g., titanium ore chlorination), processes in the pharmaceutical and food industries where careful control of the composition of the process fluid is important, if not critical.

BRIEF DESCRIPTION OF THE FIGURE

FIGURE is a schematic diagram of a cleaning system of this invention for use in a continuous process.

DETAILED DESCRIPTION

Figure 1:
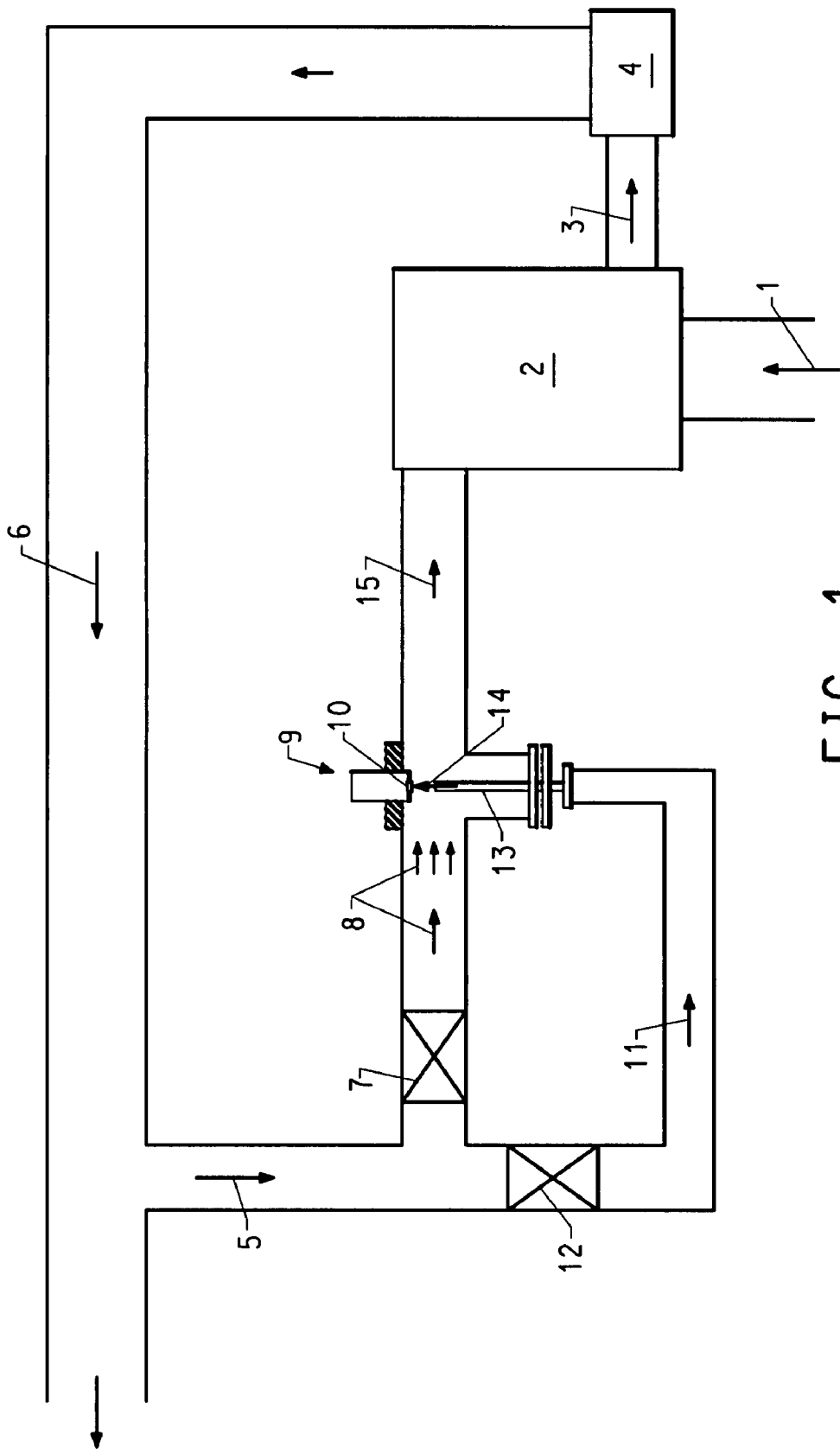

The present invention provides a system and method for cleaning in-process sensors. The present invention is extremely versatile, applicable in nearly all process environments where in-process sensors are used for measurements of process conditions and compositions. The cleaning system can be used in batch or continuous processes. The cleaning system is not limited by temperature, pressure, or chemical environment so long as appropriate equipment for such condition is utilized, which can readily be determined by those skilled in the art. Indeed, specific advantages of the cleaning system relate to its utility in highly corrosive environments, wherein the fluid is highly viscous and erosive.

The cleaning system of this invention enables the removal of contaminants, such as organic growth, solids, gels, films or coatings comprising gaseous or liquid phases, from the surface of an in-process sensor. An in-process sensor is defined herein as an analytical instrument, which interacts with a process fluid, resulting in a measurement of one or more characteristics of the fluid and its components. Furthermore, by "in-process" it is meant herein to encompass large manufacturing operations, such as processing plants for commodity chemicals, as well as small scale manufacturing operations, such as those for fine chemicals and even laboratory scale syntheses. Examples of characteristics of a process fluid capable of being measured include electrical characteristics such as pH or conductivity and the concentration of one or more chemical components of the fluid. The sensor may also be part of a vessel through which the instrument transmits, such as a nuclear magnetic level device. This invention is particularly advantageous when used to clean sensors which measure concentrations of at least one component of the process fluid.

Examples of in-process sensors suitable for use with the cleaning system of this invention include electrodes, such as pH meters and dissolved oxygen analyzers, membranes, nuclear density and level gauges, and spectroscopic instruments, including Infrared, Raman, and Near Infrared instruments and particle size detectors. The spectroscopic instruments may use cells or probes. The preferred sensor for any particular application will depend on the process, that is, the equipment being used, operating conditions (temperature, pressure), the characteristic being measured, chemical composition, reactor vessel design, etc.

The cleaning system of this invention is particularly advantageous when Infrared, Raman or Near Infrared spectroscopic instruments are used for composition measurements. When such instruments are used, probes are preferred over cells. In a particular application, for composition measurements of a process fluid in the chlorination of titanium ores, use of an Infrared spectroscopic probe is preferred. More preferably, for this application, the probe is a Fourier transform infrared probe (FTIR), and most preferred is a FTIR attenuated total reflectance (ATR) probe. Preferably the ATR probe has a diamond or sapphire window exposed to the process fluid. For use with process fluids from the chlorination of titanium ores, the preferred window is a diamond window, which introduces less interference in the desired spectroscopic range.

In the cleaning system of this invention, the sensor has a surface which is in contact with a process fluid. "Surface" of the sensor is meant herein to include windows of spectroscopic instruments as well as windows on reaction vessels through which an electromagnetic signal may pass to generate a measurement, electrode surfaces, cell walls, and the like. Contact of the process fluid with the sensor may occur by passing the fluid through a pipe upon which the sensor, such as a spectroscopic probe, is mounted, or by inserting the sensor, such as an electrode, into the process fluid in a reaction vessel, for example through a valve or flange. The sensor may contact the process fluid through a port in a main reaction vessel, such as a stirred tank or a pipe or continuous stirred tank reactor (CSTR) in a continuous process. Frequently, the sensor will contact the process fluid through a side stream from a main process fluid, for example through a sampling system.

By "process fluid" it is meant herein the contents of a reaction vessel. The process fluid may comprise a liquid and/or a gas and often will contain entrained solids. In a continuous process, the process fluid may be in the form of a process stream flowing through a pipeline reactor or one or more of a series of continuous stirred tank reactors. The process fluid may be in the form of solution or slurry in a batch reaction vessel, such as a stirred tank. In a batch process, there is further provided a pump, which may be located within a batch reaction vessel or external to the vessel through which to transfer process fluid to the jet.

The scouring jet of this invention is a vessel, such as a pipe, from which a fluid is emitted wherein the fluid, upon being emitted, expands into the environment immediately surrounding the outlet of the jet and decelerates. The scouring jet has an inlet in contact with the process fluid and through which the fluid enters the jet and an outlet from which the fluid is emitted. The jet inlet may be in contact with the process fluid directly from the reaction vessel. More commonly, and preferably, a side stream from the reaction vessel is used to direct a portion of the process fluid to the jet inlet.

It should be recognized that the primary function of the fluid directed to and emitted from the scouring jet is to clean the sensor surface. Even though the jet directs fluid toward the sensor, and the sensor may measure a characteristic of this fluid, a separate flow of fluid, different from the jet flow is generally the main source of measurement for the sensor.

The outlet of the scouring jet may be comprised of a single nozzle or multiple nozzles from which the fluid is emitted. The jet outlet is smaller in diameter than the vessel into which the jet discharges the fluid. Decreasing the size (diameter) of the outlet, results in increasing the velocity of flow from the jet. The shape of the outlet nozzle(s) may be designed in any shape suitable to clean the surface of the sensor. For example, a small single optical window or electrode may be effectively cleaned by a nozzle having a small round shape. A large optical window or membrane may be effectively cleaned by a nozzle with a large diameter, a slot-shaped nozzle, or even multiple small round-shaped nozzles.

The scouring jet is positioned relative to the sensor such that discharge of the process fluid from the jet outlet impinges on the surface of the sensor in contact with the process fluid. The distance of the jet outlet from the sensor depends on the conditions into which the fluid is emitted and the geometry and dimensions of the jet, including those of the jet outlet, angle of emission from the jet relative to the sensor and relative to a process flow direction, and others. Such parameters can be optimized using standard engineering calculations. In one particular application, that is, wherein the sensor measures composition of a process fluid in chlorination of titanium ores, the jet outlet is positioned between 0.25 and 1.0 inches from the sensor surface.

The angle at which the jet flow impinges on the sensor surface is in the range of 0° to 90°, where 0° is parallel to the sensor surface and 90° is perpendicular to the sensor surface, preferably 45° to 90°. The preferred angle and distance between the jet and the sensor may be determined experimentally or by calculations so that for a given geometry and velocity the desired degree of cleaning will be achieved. Harder contaminants and smaller sensor surfaces are better suited to impingement at higher angles, that is, perpendicular to the sensor surface. Softer contaminants and larger sensor surfaces may be better suited to impingement at lower angles, that is, more parallel to the surface. When the sensor is a flow-through spectroscopic cell, where a perpendicular jet would interfere with the spectroscopic light beam, placing the jets at an angle less than 90° is desirable, to limit jet interference with equipment surrounding the sensor.

It should be recognized that flow of fluid through the jet need not be continuous. Valves may be positioned to permit or prevent or control flow of fluid through the jet. For example, a valve may isolate the process fluid from the sensor, if it is desired to discontinue the measurement during the cleaning process. Alternatively, a valve may isolate the scouring jet from the process fluid, in order to operate the cleaning system on a less than continuous, that is, periodic, basis. Furthermore, volumetric flow of process fluid through the jet may be controlled by using valves. Such valves may be operated manually or preferably, automatically. The valves selected should provide good control of flow and be durable. For example, for use with process fluids comprising solid particulates, erosion resistant valves, such as those with ceramic liners are effective.

Process equipment surrounding the sensor is preferably made from materials that are erosion resistant. If easily abraded materials have been used, such materials are preferably coated with hard-facing or shielded with a hard, erosion resistant material. In addition, the pipe or vessel into which the sensor is inserted is preferably sufficiently large so the velocity of fluid exiting the jet can drop rapidly after impact with the sensor in order to minimize potential for damage to equipment surrounding the sensor which may be impacted by the jet flow deflected after impact with the sensor.

During operation of the cleaning system of this invention, movement of the process fluid through the system may induce vibration due to design of the scouring jet, sensor and process lines through which the fluid passes. This vibration may be detrimental to measurement accuracy. Preferably means should be take to avoid the vibration such as, stiffening the jet, bracing the sensor chamber and placing flow obstructions, such as valves and elbows in the process vessels at a distance from the sensor and jet. Preferably any obstruction is located at least 10 diameter measures upstream and 5 or more diameters downstream of the jet.

The method of this invention comprises directing at least a portion of a process fluid to a scouring jet. It should be recognized that the flow of process fluid to the jet can be controlled independently from the flow of fluid to the sensor. The portion of the process fluid directed to the jet can be as much as 100% of the entire process fluid flow, but preferably is less than 50%. Directing 100% of the process fluid flow to the jet may be advantageous when the sensor surface is so contaminated that the objective is to clean the surface until the contamination is sufficiently reduced and/or eliminated. When a portion of the process fluid is directed to the jet, the portion is typically separated from the main process fluid as a side stream, especially using sample system principles. The portion of the fluid directed to the jet is discharged from the jet such that the fluid impinges on the sensor surface, thereby cleaning the surface. Both the velocity of the jet as well as any suspended solids present in the process fluid provide scouring action to clean the sensor.

The method of this invention may be performed continuously during operation of the sensor, or intermittently, based on a periodic schedule, especially if the rate of fouling is well understood, or on an as-needed basis, that is, when fouling of the sensor is either suspected or detected. The method of this invention may be controlled with respect to duration of the cleaning, if cleaning is not performed continuously, as well as with respect to intensity of the cleaning, such as due to velocity of the fluid discharged from the jet.

The duration of a cleaning cycle, when intermittent cleaning is practiced may be from as short as a few seconds to many hours. The fraction of time cleaning occurs during process operation may be less than 1% of the time to as much as 100% of the time. To minimize potential for erosion of the sensor surface, preferably duration of cleaning should continue only as long as necessary to remove the contaminants.

The intensity of the process fluid exiting the jet should be sufficient to remove the contaminants, that is, to clean the sensor surface. However, consideration must be given to minimize damage to the sensor and its surrounding environment. Intensity is a function of velocity of the jet, in addition to the characteristics of the process fluid, distance of the jet outlet from the sensor and other factors, including, for example, hardness of particulate materials in the process fluid.

The preferred jet velocity may range from a few inches per second to several hundred feet per second. In operation, the preferred velocity will depend on the composition and characteristics of the process fluid, distance of the jet outlet from the sensor, and other factors such as hardness of the contaminant, durability of the sensor surface, which can be determined by experimental optimization.

It may be desirable to treat the portion of the process fluid from the main process fluid. Such treatment may involve, for example, heating or cooling the process fluid, vaporizing a condensed process fluid, or removing or adding particulate matter to the fluid. It may be particularly desirable to remove particulate matter that may be particularly abrasive. Particulate matter may be removed, for example, by means such as filters, cyclone separation. However, it should be recognized there is reduced scouring absent particulates in the fluid.

In a preferred embodiment of this invention, the cleaning system of this invention further comprises a control strategy. The control strategy may provide for independent adjustment of the intensity, frequency and duration of the cleaning operation. Thus, a high level of control over the cleaning system is provided. The sensor may provide a measurement of a characteristic of a contaminant that obstructs or obscures the sensor in addition to measuring the desired characteristic of the process fluid. Spectroscopic probes are the preferred sensors for this mode of operation, more preferably Infrared probes, and most preferably, FTIR ATR probes. In one example of a control strategy, the sensor provides a measurement of a characteristic of the contaminant, wherein the measurement relates to the concentration of the contaminant, and compares the measurement with a predetermined set point. Operation of the scouring jet is modified in a manner to maintain or reduce the concentration of solids or contaminants below the set point.

An important advantage of this process is that the cleaning method can be operated while the sensor continues to monitor the process and perform the measurements. This is particularly useful when the sensor is being used in classical continuous feedback control operation.

The cleaning system and method of this invention has particular utility in process operations, using in-process spectroscopic probes, especially Infrared probes, such as the process described in U.S. Pat No. 6,562,312 issued on May 13, 2003, the teachings of which are hereby incorporated by reference. For example, in the process for making titanium dioxide, the present invention may be used in the chloride or the sulfate process to control or monitor steps in the process including controlling or monitoring in chlorination, oxidation, finishing or in precipitation and finishing, respectively.

In addition, manufacturing processes in the pharmaceutical and biological materials industries are particularly suitable to include the use of the present invention. For example, the present invention is directly applicable to these and other processes where maintaining the integrity of the process stream is a consideration. Integrity may be paramount for a process that cannot tolerate the smallest contaminant or to protect operators from contact with a process that may contain highly toxic, such as carcinogenic or mutagenic, materials or organisms.

EXAMPLES

Example 1

The following specific example describes in detail a typical installation and operation of the cleaning system and cleaning method of this invention for a continuous process operation, with reference to the FIGURE. The arrows within the piping in the FIGURE indicate the direction of flow of the process fluid. In this example, a scouring jet is used to clean the window of an attenuated reflectance FTIR probe measuring impurities in a crude titanium tetrachloride stream in accordance with U.S. Pat No. 6,562,312 issued on May 13, 2003.

A process fluid (1) derived from a fluid bed chlorinator, which comprised a mixture of metal chlorides and oxychlorides and suspended solid particles in a process to manufacture titanium tetrachloride was fed to a reaction vessel (2). This fluid was treated with water to passivate the aluminum chloride present (not shown) and the treated fluid (3) was transferred using pump (4) from vessel (2) to main process flow (6).

A portion of the treated fluid (5) was removed from the main process flow (6). With valve (7) open, a main sample flow of treated process fluid (8) was directed to an Infrared analyzer (9) as a side stream. The analyzer comprised a diamond window (10) which contacted the process fluid (8) and recorded a measurement, which was transmitted to a feedback controller (not shown) to control the amount of water added (not shown).

A secondary flow of treated process fluid (11) was directed through open valve (12) to a scouring jet (13). Ceramic valves (7) and (12) were controlled using a feedback loop to adjust flow between main sample flow (8) and flow to scouring jet (11). Fluid (11) exited scouring jet (13) through a nozzle (14), which was round in shape and directed at an angle of 90° and a distance of between 0.25 and 1.0 inches toward window (10) of analyzer (9), resulting in a scouring effect to remove solid particulates and generating combined sample flow (15), which was fed into reaction vessel (2).

Example 2

The following specific example describes in detail a typical installation and operation of the cleaning system and cleaning method of this invention for a batch process operation.

A Fourier Transform Infrared probe is placed in a recycle loop on a stirred tank reaction vessel used in a fermentation process where the fermentation mixture is the process fluid. A recycle pump is used to remove fluid from the reaction vessel, cycle through a sample system where spectroscopic measurements are made to monitor the composition of the process fluid. A side stream is removed from the recycle loop and is fed to a scouring jet. The process fluid is discharged from the scouring jet with sufficient kinetic energy, derived from the pressure and flow rate generated by the pump, to clean the spectroscopic probe.

Example 3

The cleaning system and method of this invention can be applied to analysis of fluid using flow-through infrared analyzer cell. A fluid undergoes Infrared spectroscopic analysis in a standard flow through cell. The fluid sample flows in the bottom of the cell, and exits through the top of the cell. Windows on either side of the cell permit the Infrared beam to enter one window, pass through the cell and exit the opposite window to a detector. Solids in the stream adhere to the windows requiring continuous removal to permit accurate analysis of the fluid composition.

A pressurized stream of the fluid being analyzed is supplied to two scouring jets entering the sample cell below each window and oriented so that they impact the window at an angle of approximately 45°. This angle permits the jets to be positioned outside the infrared beam path. Velocity through the jets is controlled by manual adjustment of valves in the lines leading to each jet. Optimum velocity is determined experimentally, by slowly opening the valves until the solids coating the window are removed.

Example 4

The cleaning system and method of this invention can be applied to analysis of a liquid in a tank using a pH probe using a single jet to clean both a glass and reference electrode. A pH probe is inserted through a port in the side wall of an agitated tank containing a liquid in which a batch chemical reaction is taking place, producing gelatinous solids, which collect on the surface of the pH probe electrodes. The solids on the electrodes cause errors in measurements by the pH probe of the liquid in the tank as the reaction takes place.

The glass and reference electrodes of the pH probe are both flat surfaces and are adjacent, together covering an area of about 0.75 inches in diameter.

In order to clean the surfaces of the electrodes, liquid is withdrawn from the tank into a centrifugal pump with a variable-speed drive. The liquid exiting the pump flows through a pipe passing through the same port used to insert the pH probe into the tank. The flow exits through a scouring jet nozzle at the end of this pipe at an angle of approximately 5°, that is, nearly parallel to the electrode surfaces, and the flow impinges upon the surfaces of the electrodes.

The speed of the pump is increased to increase scouring jet velocity, and thus scouring intensity increases as the reaction proceeds and the generation of solids increases. The speed necessary to provide adequate cleaning at each phase of the reaction is determined experimentally. Once an acceptable pump speed profile is determined, the same profile is used for each subsequent time this particular chemical reaction is performed in the tank.

The Examples provided herein are illustrative and should not be construed as limiting the scope of the invention. Variations will be readily appreciated by those skilled in the art.

What is claimed is:

1. A method for cleaning an in-process sensor for a process in which a surface of the sensor is exposed to one or more contaminants, comprising:
   (a) providing a reaction vessel having an interior region and having a process fluid located therein, wherein the process fluid is selected from the group consisting of biological, pharmaceutical and hazardous material;
   (b) positioning the surface of the sensor on the interior region of the reaction vessel such that the surface of the sensor is capable of contacting the process fluid and having a build up of the contaminants thereon, the region surrounding the sensor being coated with hard-facing material, the sensor being an infrared or near-infrared probe; wherein the contaminants comprise liquid and gaseous phases; and
   (c) providing a scouring jet having an inlet in contact with the process fluid and through which the process fluid enters the jet and an outlet from which the process fluid is emitted, the outlet of the scouring jet being positioned so that the process fluid is emitted in a direction toward the surface of the sensor to impinge on the surface of the sensor whereby the impinging process fluid has a scouring action capable of removing one or more of the contaminants from the surface of the sensor;
   and wherein the process fluid emitted from the scouring jet does not contain a cleaning fluid.

2. The method of claim 1 in which the contaminant is selected from the group consisting of organic growth, solids, gels, films, and coatings.

3. The method of claim 1 further comprising adjusting the intensity, frequency and duration of process fluid emitted from the scouring jet.

4. The method of claim 1 in which the reaction vessel is a pipeline reactor.

5. The method of claim 1 in which the reaction vessel is a stirred tank reactor.

6. The method of claim 1 in which the process fluid comprises entrained solids.

7. The method of claim 1 in which the outlet of the scouring jet comprises a single nozzle or multiple nozzles.

8. The method of claim 1 in which the reaction vessel is for a pharmaceutical process.

9. The method of claim 1 in which the reaction vessel is for processing biological materials.

10. A method for making titanium dioxide in a reaction vessel comprising an in-process sensor in which a surface of the sensor is exposed to one or more contaminants of the titanium dioxide process, comprising:
    (a) providing the reaction vessel having an interior region and having a process fluid for making titanium dioxide located therein;
    (b) positioning the surface of the sensor on the interior region of the reaction vessel such that the surface of the sensor is capable of contacting the process fluid and having a build up of the contaminants thereon, the region surrounding the sensor being coated with hard-facing material, the sensor being an infrared or near-infrared probe; wherein the contaminants comprise liquid and gaseous phases; and
    (c) providing a scouring jet having an inlet in contact with the process fluid and through which the process fluid enters the jet and an outlet from which the process fluid is emitted, the outlet of the scouring jet being positioned so that the process fluid is emitted in a direction toward the surface of the sensor to impinge on the surface of the sensor whereby the impinging process fluid has a scouring action capable of removing one or more of the contaminants from the surface of the sensor; and wherein the process fluid emitted from the scouring jet does not contain a cleaning fluid.

11. The method of claim 1 wherein the probe comprises a diamond window.

12. The method of claim 10 wherein the probe comprises a diamond window.

13. The method of claim 1 wherein the process fluid comprises suspended solids for providing scouring action.

14. The method of claim 10 wherein the process fluid comprises suspended solids for providing scouring action.

15. A method for cleaning an in-process sensor for a process in which a surface of the sensor is exposed to one or more contaminants, comprising:
    (a) providing a reaction vessel having an interior region and having a process fluid located therein, wherein the process fluid is selected from the group consisting of biological, pharmaceutical and hazardous material;
    (b) positioning the surface of the sensor on the interior region of the reaction vessel such that the surface of the sensor is capable of contacting the process fluid and having a build up of the contaminants thereon, the region surrounding the sensor being coated with hard-facing material or shielded with a hard, erosion resistant material, wherein the contaminants comprise liquid and gaseous phases;; and
    (c) providing a scouring jet having an inlet in contact with the process fluid and through which the process fluid enters the jet and an outlet from which the process fluid is emitted, the outlet of the scouring jet being positioned so that the process fluid is emitted in a direction toward the surface of the sensor to impinge on the surface of the sensor whereby the impinging process fluid has a scouring action capable of removing one or more of the contaminants from the surface of the sensor; wherein the process fluid emitted from the scouring jet does not contain a cleaning fluid, and wherein the cleaning of the sensor surface and operation of the sensor may occur simultaneously.

* * * * *